US012562236B2

(12) United States Patent
Wu et al.

(10) Patent No.: US 12,562,236 B2
(45) Date of Patent: Feb. 24, 2026

(54) DESIGNING AND FOLDING STRUCTURAL PROTEINS FROM THE PRIMARY AMINO ACID SEQUENCE

(71) Applicants:INTERNATIONAL BUSINESS MACHINES CORPORATION, Armonk, NY (US); MIT Massachusetts Institute of Technology, Cambridge, MA (US)

(72) Inventors: Lingfei Wu, Elmsford, NY (US); Siyu Huo, White Plains, NY (US); Tengfei Ma, White Plains, NY (US); Pin-Yu Chen, White Plains, NY (US); Zhao Qin, Lynnfield, MA (US); Eugene Jungsup Lim, Cambridge, MA (US); Francisco Javier Martin-Martinez, Grenada (ES); Hui Sun, Cambridge, MA (US); Benedetto Marelli, Lexington, MA (US); Markus Jochen Buehler, Boxford, MA (US)

(73) Assignees: International Business Machines Corporation, Armonk, NY (US); Massachusetts Institute of Technology, Cambridge, MA (US)

( * ) Notice: Subject to any disclaimer, the term of this patent is extended or adjusted under 35 U.S.C. 154(b) by 796 days.

(21) Appl. No.: 16/585,679

(22) Filed: Sep. 27, 2019

(65) Prior Publication Data
US 2021/0098074 A1     Apr. 1, 2021

(51) Int. Cl.
*G16B 5/00* (2019.01)
*G06N 3/04* (2023.01)
(Continued)

(52) U.S. Cl.
CPC ................. *G16B 5/00* (2019.02); *G06N 3/04* (2013.01); *G06N 3/08* (2013.01); *G16B 15/20* (2019.02); *G16B 40/00* (2019.02)

(58) Field of Classification Search
None
See application file for complete search history.

(56) References Cited

U.S. PATENT DOCUMENTS

| | | |
|---|---|---|
| 2004/0083061 A1 | 4/2004 | Hannah |
| 2019/0114511 A1 | 4/2019 | Gao et al. |

(Continued)

FOREIGN PATENT DOCUMENTS

| | | |
|---|---|---|
| CN | 105740646 A | 7/2016 |
| CN | 106295242 A | 3/2019 |

OTHER PUBLICATIONS

DeepPrime2Sec: Deep Learning for Protein Secondary Structure Prediction from the Primary Sequences Ehsaneddin Asgari, Nina Poerner, Alice C. McHardy, Mohammad R.K. Mofrad bioRxiv 705426; Jun. 5, 2019 (Year: 2019).*

(Continued)

*Primary Examiner* — Karlheinz R. Skowronek
*Assistant Examiner* — Joseph Pulliam
(74) *Attorney, Agent, or Firm* — Heather Schuler

(57) ABSTRACT

A method, computer system, and a computer program product for designing one or more folded structural proteins from at least one raw amino acid sequence is provided. The present invention may include computing one or more character embeddings based on the at least one raw amino acid sequence by utilizing a multi-scale neighborhood-based neural network (MNNN) model. The present invention may then include refining the computed one or more character embeddings with at least one set of sequence neighborhood information. The present invention may further include (Continued)

predicting one or more dihedral angles based on the refined one or more character embeddings.

25 Claims, 9 Drawing Sheets

Specification includes a Sequence Listing.

(51) Int. Cl.
| | |
|---|---|
| *G06N 3/08* | (2023.01) |
| *G16B 15/20* | (2019.01) |
| *G16B 40/00* | (2019.01) |

(56) References Cited

U.S. PATENT DOCUMENTS

| | | | |
|---|---|---|---|
| 2021/0098074 | A1 | 4/2021 | Wu |
| 2021/0166779 | A1 | 6/2021 | Jumper |
| 2021/0304847 | A1 | 9/2021 | Senior |

OTHER PUBLICATIONS

Min S, Lee B, Yoon S. Deep learning in bioinformatics. Brief Bioinform. Sep. 1, 2017;18(5):851-869. (Year: 2017).*

Wardah, Wafaa et al. "Protein Secondary Structure Prediction Using Neural Networks and Deep Learning: A Review." Computational biology and chemistry 81 (2019): 1-8. Web. (Year: 2019).*

Lee, J., Freddolino, P.L., Zhang, Y. (2017). Ab Initio Protein Structure Prediction. In: J. Rigden, D. (eds) From Protein Structure to Function with Bioinformatics. Springer, Dordrecht. (Year: 2017).*

Li, Haiou et al. "Deep Learning Methods for Protein Torsion Angle Prediction." BMC bioinformatics 18.1 (2017): 417-417. Web. (Year: 2017).*

Alam et al., "Variational Autoencoders for Protein Structure Prediction," In Proceedings of the 11th ACM International Conference on Bioinformatics, Computational Biology and Health Informatics, (BCB '20), Sep. 21-24, 2020, Virtual Event, USA. ACM, New York, NY, USA, 10 pages. https://doi.org/10.1145/3388440.3412471.

Anonymous Authors, "ProGAE: A Geometric Autoencoder-based Generative Model for Disentangling Protein Conformational Space", Under review as a conference paper at ICLR 2021, Sep. 28, 2020 (modified: Mar. 5, 2021), https://openreview.net/forum?id=LxhlyKH6VP, 11 pages.

Chen, et al., "Protein Structure Prediction Using Machine Learning", U.S. Appl. No. 17/842,839, filed Jun. 17, 2022, 49 pgs.

Guo et al., "Generating Tertiary Protein Structures via an Interpretative Variational Autoencoder," arXiv:2004.07119v2 [q-bio.BM] Jun. 16, 2021, 17 pages.

Kipf et al., "Variational Graph Auto-Encoders", arXiv:1611.07308v1 [stat.ML] Nov. 21, 2016, 3 pages.

Zhang et al., "Graph Neural Networks and Their Current Applications in Bioinformatics." Frontiers in Genetics, vol. 12, article 690049, Jul. 29, 2021, doi:10.3389/fgene.2021.690049, 22 pages.

"IBM Appendix P"—List of IBM Patents or Patent Applications Treated as Related, Filed herewith, 2 Pages.

Mell et al., "The NIST Definition of Cloud Computing", Recommendations of the National Institute of Standards and Technology, NIST Special Publication 800-145, Sep. 2011, 7 pages.

Alquraishi, "End-to-End Differentiable Learning of Protein Structure", Cell Systems, Apr. 24, 2019, vol. 8, Issue 4, pp. 292-301.

Evans et al., "De novo structure prediction with deep-learning based scoring", Thirteenth Critical Assessment of Techniques for Protein Structure Prediction, (Abstracts), Dec. 1-4, 2018, 2 pages.

Dill et al., "The Protein Folding Problem", Annu Rev Biophys., vol. 37, pp. 289-316, Jun. 9, 2008.

Gao et al., "Real-value and confidence prediction of protein backbone dihedral angles through a hybrid method of clustering and deep learning", arXiv:1712.07244v1, Dec. 19, 2017, pp. 1-23.

Heffernan et al., "Single-Sequence-Based Prediction of Protein Secondary Structures and Solvent Accessibility by Deep Whole-Sequence Learning", Journal of Computational Chemistry, 2018, pp. 1-7.

Kim, "Dihedral angle prediction using generative adversarial networks", Master Thesis, University of Copenhagen, Faculty of Science, Submitted Mar. 5, 2018, 72 pages.

Li et al., "Deep learning methods for protein torsion angle prediction", BMC Bioinformatics, vol. 18, No. 417, (2017) pp. 1-13.

Qin et al., "Artificial intelligence method to design and fold alpha-helix structural proteins from the primary amino acid sequence", bioRxiv preprint first posted online Jun. 5, 2019; https://www.biorxiv.org/content/10.1101/660639v1, doi: https://doi.org/10.1101/660639, 17 pages.

* cited by examiner

100

200

Start

Retrieve Sequence for Amino Acid Residue
202

Compute Character Embeddings for Each Amino Acid
204

Predict Dihedral Angles
206

Predict Secondary Structural Information
208

Visualize Current Amino Acid Embeddings Data
210

Implement Protein Structural Analysis
212

End

400

Sequence Listing of Peptide AmelF3_+1 (SEQ ID NO. 1)

Ala Ala Ala Ala Leu Lys Asn Ala Gln Gln Ala Gln Leu Asn Ala Gln 1         5               10             15

Glu Lys Ser Leu Ala Ala Leu Lys Ala Gln Ser Glu 20               25

FIG. 6

DESIGNING AND FOLDING STRUCTURAL PROTEINS FROM THE PRIMARY AMINO ACID SEQUENCE

SEQUENCE LISTING

A text file containing a sequence listing is incorporated by reference herein in its entirety. The name of the text file is P201904106US01_SequenceListing_Text_File, the date of creation of the text file is Aug. 25, 2023, and the size of the text file in bytes is 4 KB.

REFERENCE TO AN ELECTRONIC SEQUENCE LISTING

The instant application contains a Sequence Listing which has been filed electronically in an ASCII text file. The contents of the electronic sequence listing (AmelF3_plus1-20191220.txt, Size: 565 bytes, and Date of Creation: Dec. 20, 2019) is herein incorporated by reference in its entirety.

STATEMENT REGARDING PRIOR DISCLOSURES BY THE INVENTOR OR A JOINT INVENTOR

A document titled "Artificial intelligence method to design and fold alpha-helix structural proteins from the primary amino acid sequence," published on the website https://doi.org/10.1101/660639 on Jun. 5, 2019, made by one or more inventors listed in the current application, and submitted in an Information Disclosure Statement, is hereby considered a Grace Period Disclosure and recognized as an exception to 35 U.S.C. § 102(a)(1) prior art.

BACKGROUND

The present invention relates generally to the field of artificial intelligence, and more particularly to artificial intelligence software used in bioengineering, medicine and materials science applications.

With a world population that includes billions of people, food production and consumption is a robust field of innovation, interest and value. However, due to food spoilages, a vast quantity of food production and freshwater consumption are lost or wasted. Food spoilages may be caused by various factors, namely temperature changes, microbes, aging, poor handling, inadequate packaging and storage. Once a food product has spoiled, the food product may be considered unsuitable for human consumption. To reduce food spoilages, protein-based edible coatings may be applied to crops.

SUMMARY

Embodiments of the present invention disclose a method, computer system, and a computer program product for designing one or more folded structural proteins from at least one raw amino acid sequence. The present invention may include computing one or more character embeddings based on the at least one raw amino acid sequence by utilizing a multi-scale neighborhood-based neural network (MNNN) model. The present invention may then include refining the computed one or more character embeddings with at least one set of sequence neighborhood information. The present invention may further include predicting one or more dihedral angles based on the refined one or more character embeddings.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings:

FIG. 6 is a sequence listing for peptide AmelF3_+1 from a coiled coil domain of the honeybee silk protein (SEQ ID NO.1);

DETAILED DESCRIPTION

Figure 1:
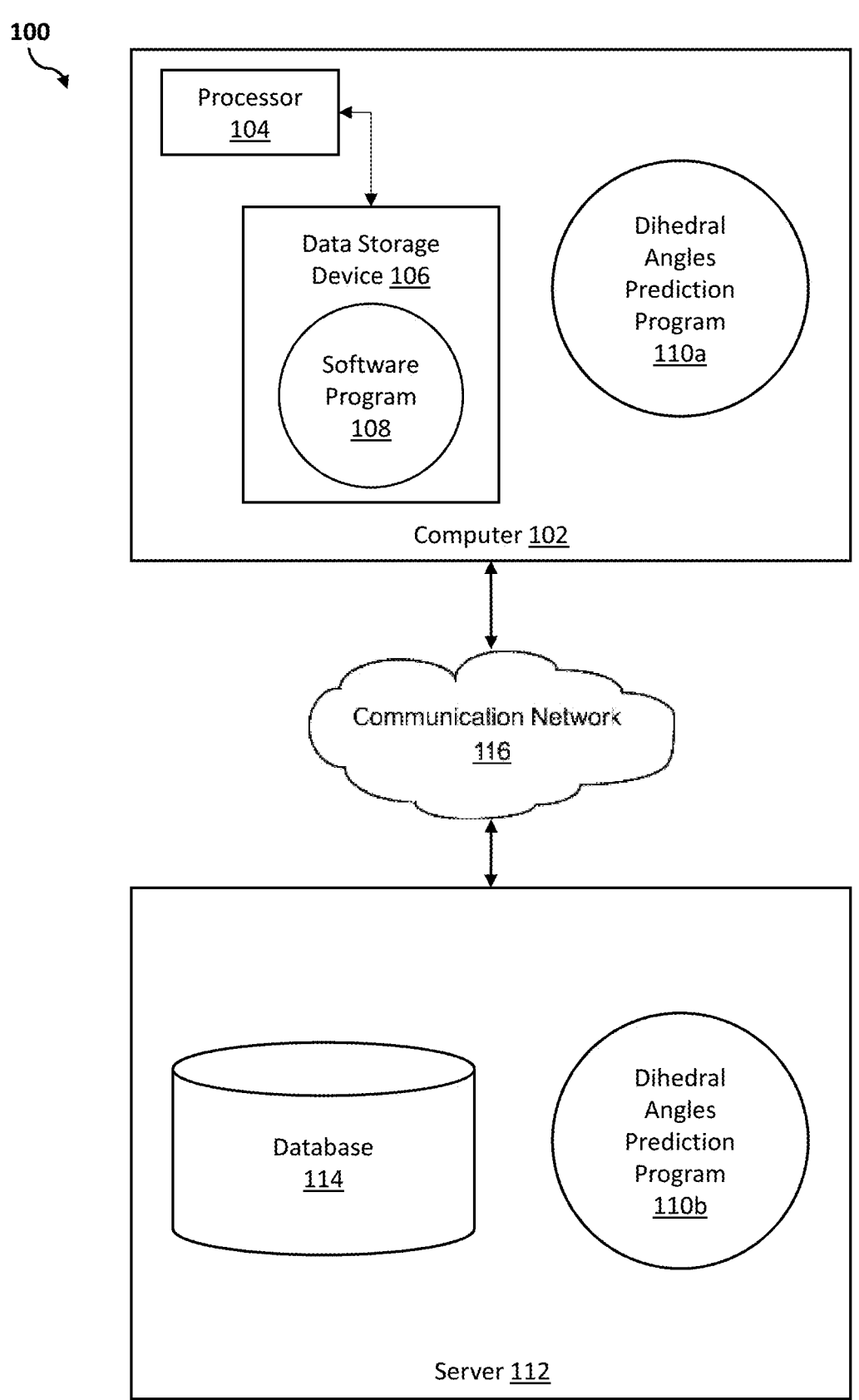
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language, Python programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for performing three dimensional (3D) structure analytics of raw amino acid protein sequence by learning multi-scale neighborhood-based artificial intelligence (AI) model for dihedral angles prediction. As such, the present embodiment has the capacity to improve the technical fields of bioengineering, medicine and materials science by utilizing a deep learning (DL) regression model for predicting dihedral angles directly from sequence neighborhood that takes into account both raw sequence neighborhood and secondary sequence neighborhood. More specifically, the dihedral angles prediction program may retrieve a sequence of amino acid residue. The dihedral angles prediction program may then compute a character embedding for each amino acid residue by using long short term memory (LSTM)/convolutional neural network (CNN) (i.e., MNNN model) (i.e., raw sequence neighborhood), and then the dihedral angles prediction program may perform dihedral angles prediction by applying additional LSTM layer. Then, the dihedral angles prediction program may predict secondary structured information (i.e., secondary sequence neighborhood) by utilizing a multilayer perceptron (MLP) layer. Then, the dihedral angles prediction program may permit iterative user interaction to visualize the current amino acid embeddings, and the dihedral angles prediction program may then perform protein structural analysis (e.g., back bone analysis, 3D geometric structure analysis, other structural analysis of the input protein sequence) based on the predicted dihedral angles.

As previously described, with a world population that includes billions of people, food production and consumption is a robust field of innovation, interest and value. However, due to food spoilages, a vast quantity of food production and freshwater consumption are lost or wasted. Food spoilages may be caused by various factors, namely temperature changes, microbes, aging, poor handling, inadequate packaging and storage. Once a food product has spoiled, the food product may be considered unsuitable for human consumption. To reduce food spoilages, protein-based edible coatings may be applied to crops.

In fact, proteins may represent the key construction materials of the living world and may offer a tremendous amount of diversity in function and, therefore, a powerful platform for potential use in bioengineering, medicine and materials science. As such, structural protein design has been utilized to prevent food spoilages and enhance food safety. Specifically, the discovery of new materials for food coating (e.g., protein-based edible coatings) may be applied to crops to reduce spoilages. However, the process for determining how to fold and design the structural proteins for an amino acid sequence with a desired property may pose challenges, specifically efficiently finding a sequence with desired property and appropriate scalability with sequence length. In traditional approaches, ad-hoc methods may be based on classical molecular dynamics (MD) simulations or experimental verification, which are unable to generalize well to a new sequence design. Additionally, with traditional approaches, time scale may be a main limitation of classical MD simulation, for accuracy and numerical stability, exponentially increasing with the length of sequences.

Furthermore, while protein domains composed of alpha helices provide extensibility and flexibility based on the many structural biomaterials (e.g., keratin and membrane proteins), there may still exist a lack of accurate and efficient tool to design protein sequence to form helical structure.

Therefore, it may be advantageous to, among other things, utilizing a deep learning (DL) regression model (i.e., multi-scale neighborhood-based neural network (MNNN) model) for predicting dihedral angles directly from sequence neighborhood by taking into account both raw sequence neighborhood and secondary sequence neighborhood. As such, a dihedral angles prediction program may be utilized to perform a three dimensional (3D) structure analytics of raw amino acid protein sequence by learning a multi-scale neighborhood-based artificial intelligence (AI) model for dihedral angles prediction. Accurate angle prediction may accelerate the process of verifying structural stability of protein sequences with less than six orders of magnitude time (e.g., from days or weeks, to second or minutes) than ab initio folding methods, and without utilizing a template, structural biological knowledge, or co-evolutional information for known protein structures.

According to at least one embodiment, the dihedral angles prediction program may include learning how to fold from an amino acid sequence. To fold from an amino acid sequence, a protein may be broken down into amino acids (i.e., the building blocks for the protein). From the amino acids, a distinct 3D organization (e.g., $\alpha$ helix, $\beta$ strand) of the amino acid sequence may be identified, and then the 3D distinct organizations may be combined to create domains (e.g., set of stable structures). As such, from the distinct amino acid sequence that provides a specific structure and function associated with the protein, the material (e.g., solid matter with distinct structure and properties) to fold the amino acid sequence may be determined. The present embodiment may include taking only raw amino acid as inputs and may directly predict dihedral angles without (i.e., in the absence of) any template, structural biological knowledge, or co-evolutional information.

According to at least one embodiment, the dihedral angles prediction program may include high throughput in silico prediction of protein structures and related material functions that provide a rational basis for the design of de novo protein materials. Therefore, achieving the capability of fast prediction of alpha-helical proteins because as one of the major universal secondary structural mortifs, alpha helices may provide a platform for materials design with wide ranging implications in a variety of application areas. For example, experimental studies reveal that $\alpha$-keratin (i.e., found in wool, hair and hooves), fish slime threads, desmin and vimentin are composed of alpha-helices, and are thus stretchable and tough protein materials.

According to at least one embodiment, a Multi-scale Neighborhood-based Neural Network (MNNN) model may be trained and utilized by the dihedral angles prediction program. A custom script may be developed to obtain phi-psi dihedral angle and sequence information for each of the natural protein structures composed of only standard amino acids that are currently available in a protein database (e.g., Protein Data Bank (PDB)). Using the dictionary of protein secondary structure predictions (DSSP) to compute the phi-psi angles of the backbone by reading the 3D structure files that are automatically downloaded from the protein database (e.g., PDB) and using a software program (e.g., open source Unix software) to build a highly structured database for training. The present embodiment may include a post-process script to take the phi-psi angle as predicted by MNNN model to combine the rest of the geometric parameters given by intrinsic coordinates within the Chemistry at Harvard Macromolecular Mechanics (CHARMM) force field to build the all-atom protein structure (i.e., folded structural protein), which may run energy minimization and molecular dynamics to validate the thermal stability of the folded structural protein.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a dihedral angles prediction program 110a. The networked computer environment 100 may also include a server 112 that is enabled to run a dihedral angles prediction program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 5, server computer 112 may include internal components 902a and external components 904a, respectively, and client computer 102 may include internal components 902b and external components 904b, respectively. Server computer 112 may also operate in a cloud computing service model, such as Software as a Service (SaaS), Analytics as a Service (AaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the dihedral angles prediction program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the dihedral angles prediction program 110a, 110b (respectively) to predict accurate dihedral angles to accelerate the process of verifying structural stability of protein sequences. The dihedral angles prediction method is explained in more detail below with respect to FIGS. 2-6.

Figure 2:
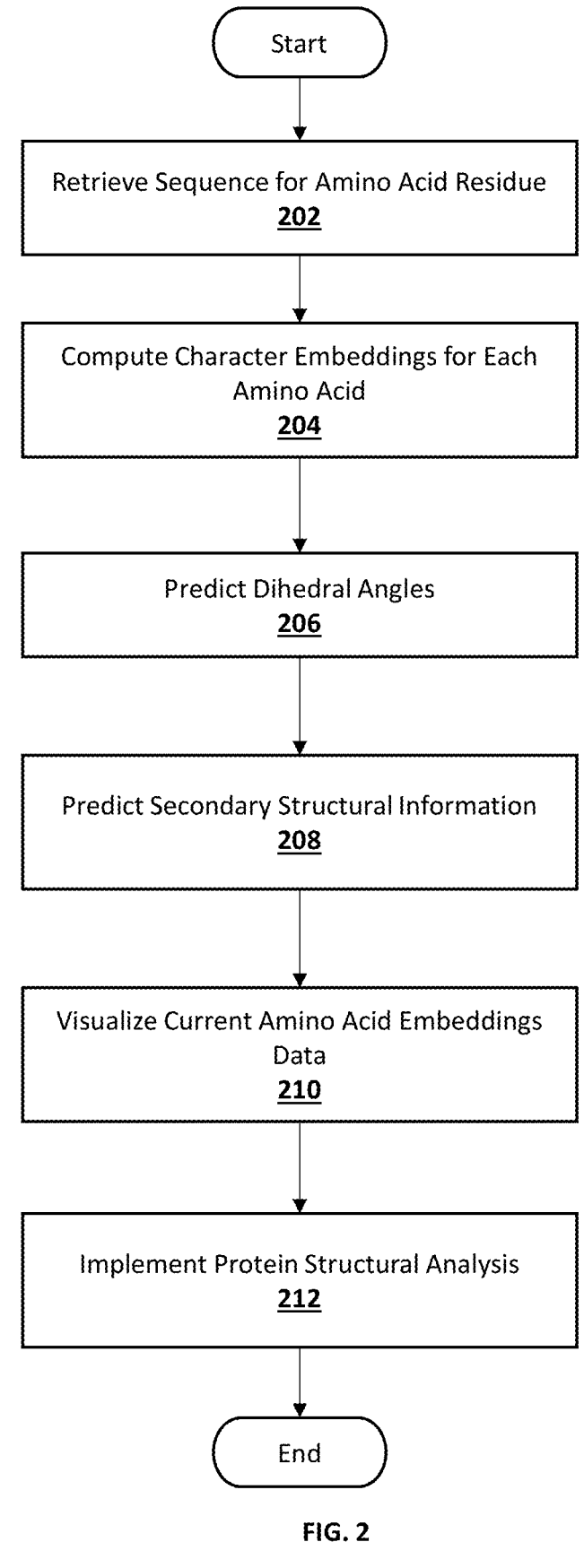
FIG. 2 is an operational flowchart illustrating a process for predicting dihedral angles according to at least one embodiment.

Referring now to FIG. 2, an operational flowchart illustrating the exemplary dihedral angles prediction process 200 used by the dihedral angles prediction program 110a, 110b according to at least one embodiment is depicted.

At 202, a sequence of amino acid residue is retrieved. Utilizing the software program 108 on the user's device (e.g., user's computer 102), a data file that includes at least one sequence of the amino acid residue (e.g., primary raw amino acid sequence) may be automatically received as input into the dihedral angles prediction program 110a, 110b via the communications network 116. The data file with the at least one sequence of the amino acid residue may be retrieved from a protein database, lab synthesis, or generated by another software program. An amino acid sequence (e.g., string of protein or peptide molecules in a particular order) may include a unique linear structure of amino acids. In at least one embodiment, a user may manually input data associated with the at least one sequence of amino acid residue into the dihedral angles prediction program 110a, 110b by manually uploading data associated with a particular amino acid sequence from a storage device.

For example, User A transmits the following protein sequence for AmelF3_+1 to the dihedral angles prediction program 110a, 110b:

AAAALKNAQQAQLNAQEKSLAALKAQSE

AmelF3_+1 is a peptide of 28 amino acids that from the coiled-coil domain of the *Apis mellifera* silk protein (AmelF3) associated with a honeybee that User A selected from a lab synthesis. A detailed sequence listing of the peptide AmelF3_+1 will be illustrated in greater detail below with respect to FIG. 6 (SEQ NO ID. 1).

Next, at 204, character embeddings for each amino acid is computed. The sequence of amino acid residue (i.e., raw amino acid sequence, raw sequence neighborhood) may be fed into an embedding layer of a Multi-scale Neighborhood-based Neural Network (MNNN) model (e.g., bidirectional long short term memory (Bi-LSTM)—neural network (e.g., convolutional neural network (CNN)/recurrent neural network (RNN)) model). For the Bi-LSTM layer, the two copies of the hidden layer may be created in which the first copy may be an "as-is" on the input sequence, and the second copy may be a reversed copy of the input sequence, both timesteps in the input sequence may still be processed one at a time, thereby resulting in faster and fuller learning on the input sequence. The Bi-LSTM may then compute the character embeddings for each primary amino acid from the feature representation learned from the Bi-LSTM—neural network structure. The computed character embeddings may improve generalization (e.g., amino acids with similar context may have nearby vectors) and reduces ML model complexity (e.g., feature detectors may only have 16 weights for every character as opposed to 256).

In at least one embodiment, each amino acid may be treated as a character. Then, existing char-embedding (i.e., character embedding) techniques may apply to compute the character embeddings of the raw amino acid. As such, the first layer of the Char CNN component of a ML model may translate the characters of the raw amino acids transmitted as input into character embeddings, which may be passed up through convolutional filters.

In at least one other embodiment, the dihedral angles prediction program 110a, 110b may utilize a long-short term memory layer (LSTM) to compute the character embeddings for each amino acid. In some embodiments, the dihedral angles prediction program 110a, 110b may utilize other character embedding computation techniques (e.g., fasttext, glove, word2vec, or transformer) to leverage features with similar protein structures to appear in other amino acid sequences.

Then, the dihedral angles prediction program 110a, 110b may apply a CNN layer to take into account sequence neighborhood information based on the computed character embeddings of each amino acid thereby generating refined character embeddings for the amino acid sequence through the use of natural language processing (NLP) techniques (e.g., entity extraction, relation extraction and classification, sentiment analysis, topic categorization) associated with the CNN layer. As such, multiple convolution filters associated with the CNN layer may slide over amino acid in the form of rows in a matrix. The dihedral angles prediction program 110a, 110b may then apply a max-pooling layer in which a max operation may be applied to the result of each filter to yield a single number for each filter to provide a fixed size output matrix and reduce output dimensionality (e.g., retaining the most salient information thereby retaining information about whether or not the feature appears and omitting information about the exact location of the information). Then, the resulting output of the pooling layer may be fed into a classifier to normalize the resulting output of the pooling layer. The output of the CNN layer may be combined to compute the refined character embeddings for each amino acid.

In at least one embodiment, the resulting output of the pooling layer may be fed into a SoftMax classifier in which the single number yielded for each filter may be normalized into a probability distribution consisting of K probabilities proportional to the exponentials of the input values by utilizing a softargmax or normalized exponential function.

In at least one other embodiment, once the dihedral angles prediction program 110a, 110b computes the character embeddings (d-dimension) for each amino acid, the raw amino acid sequence (total n number of amino acid) may be a matrix in which the size is: n×d. Each row of the matrix may correspond to one token (e.g., an amino acid) that may be a character. As such, each row may be a vector that represents an amino acid. Then, the CNN may be utilized to leverage the sequence neighborhood information as context to learn a refined character embedding.

In at least one other embodiment, the computed character embedding for each amino acid may leverage sequence neighborhood information as context, using spatial aggregation techniques (e.g., CNN), to learn a refined character embedding associated with each amino acid.

In some embodiments, the CNN layer may be utilized for part of speech tagging, without any pre-trained character embeddings. For example, for a large dataset (e.g., millions of pieces of data), the dihedral angles prediction program 110a, 110b utilizes a neural network with a sum of nine layers, and applies sentiment analysis and text categorization tasks to the input. As such, the results may learn directly from the character-level inputs. In another embodiment, the dihedral angles prediction program 110a, 110b may apply character-level convolutions to a ML model, using the output of the character-level CNN as input to an LSTM at each time step.

Continuing with the previous example, the AmelF3_+1 is fed into a MNNN model, where the AmelF3_+1 is broken down into the individual 28 amino acids that are treated as a character. Then, the LSTM layer is utilized to translate each character into a character embedding. Each character embedding associated with each of the 28 amino acids are then fed into a CNN layer in which each embedding is further filtered by multiple convolution layers, yielding a single number from the max pooling layer, and normalized by the SoftMax classifier. Therefore, refining the character embeddings for each of the 28 amino acids.

Then, at 206, the dihedral angles are predicted. Based on the refined character embeddings of amino acid sequence, the dihedral angles prediction program 110a, 110b may apply another LSTM layer to perform one or more predictions for one or more dihedral angles. For the first amino acid, the LSTM layer may utilize a hidden representation (i.e., hidden layer) to predict the dihedral angles. For the second and subsequent amino acids, the dihedral angles prediction program 110a, 110b may augment (or refine) the embeddings of the current amino acids by utilizing algorithms (e.g., K-means clustering, Mean Squared Error as a loss function) of predicted secondary structure character and then may predict the dihedral angles.

Continuing with the previous example, the refined character embeddings associated with each of the 28 amino acids are then fed into another LSTM layer to predict the dihedral angles associated with AmelF3_+1. By utilizing K-means clustering, the dihedral angles associated with the first amino acid structure from AmelF3_+1 is predicted. Then, K-means clustering is used on next amino acid until the dihedral angles associated with each of the 28 amino acids are predicted.

Then, at 208, secondary structural information is predicted. The dihedral angles prediction program 110a, 110b may utilize a multilayer perception (MLP) layer for predicting the secondary structured information (i.e., secondary sequence neighborhood). Once the dihedral angles are predicted, the dihedral angles prediction program 110a, 110b may compute secondary character embeddings to further predict secondary structure characters as additional constraints for the MNNN model to achieve a better angle prediction by incorporating the short-term and long-term spatial dependency of each amino acid (e.g., if one amino acid is alpha helix (one secondary structure). As such, the secondary character embeddings may be passed as an additional input for formulating the final embedding for predicting dihedral angles associated with the next amino acid transmitted as input into the MLP layer by the dihedral angles prediction program 110a, 110b.

Additionally, in the computational biology domain, there may be a determined (e.g., eight) quantity of different secondary structure characters in total. The dihedral angles prediction program 110a, 110b, however, may be large areas that are not fully covered by such a categorization. As such, the dihedral angles prediction program 110a, 110b may utilize a data-driven approach, such as clustering techniques (e.g., K-mean clustering) to compute a possible number of secondary structure characters (or classifications).

Continuing with the previous example, the dihedral angles prediction program 110a, 110b then uses K-mean clustering to compute the number of secondary structure characters, and therefore, compute secondary character embeddings associated with AmelF3_+1.

Then, at 210, current amino acid embeddings data is visualized. The dihedral angles prediction program 110a, 110b may utilize embedding visualization tools (e.g., t-Distributed Stochastic Neighbor Embedding (t-SNE)) to visualize the current amino acid embeddings. The dihedral angles prediction program 110a, 110b may allow iterative user interaction to visualize the quality of current amino acid embeddings and/or angle predictions.

In at least one embodiment, the dihedral angles prediction program 110a, 110b may provide an easy way to monitor the predicted dihedral angles by utilizing real-time user interaction in which the dihedral angle predictions may be presented to one or more subject matter experts (SMEs). The SMEs may utilize domain expertise as feedback to modify the dihedral angle prediction and may send back the dihedral angle predictions to the dihedral angles prediction program 110a, 110b for another round of predictions.

Continuing with the previous example, the various current amino embeddings and structure associated with AmelF3_+1 is displayed for the user via t-SNE.

Then, at 212, protein structural analysis is implemented. The dihedral angles prediction program 110a, 110b may utilize protein structural analysis (e.g., back bone analysis, three dimensional (3D) geometric structure analysis) and other structural analysis of the input protein sequence to run protein structure physical simulations (e.g., molecular dynamic (MD) simulations).

Continuing with the previous example, the dihedral angles prediction program 110a, 110b then utilizes the 3D geometric structure analysis to generate the folded 3D protein structure associated with AmelF3_+1 based on the current amino acid embeddings and the AmelF3_+1 structure.

Figure 3:
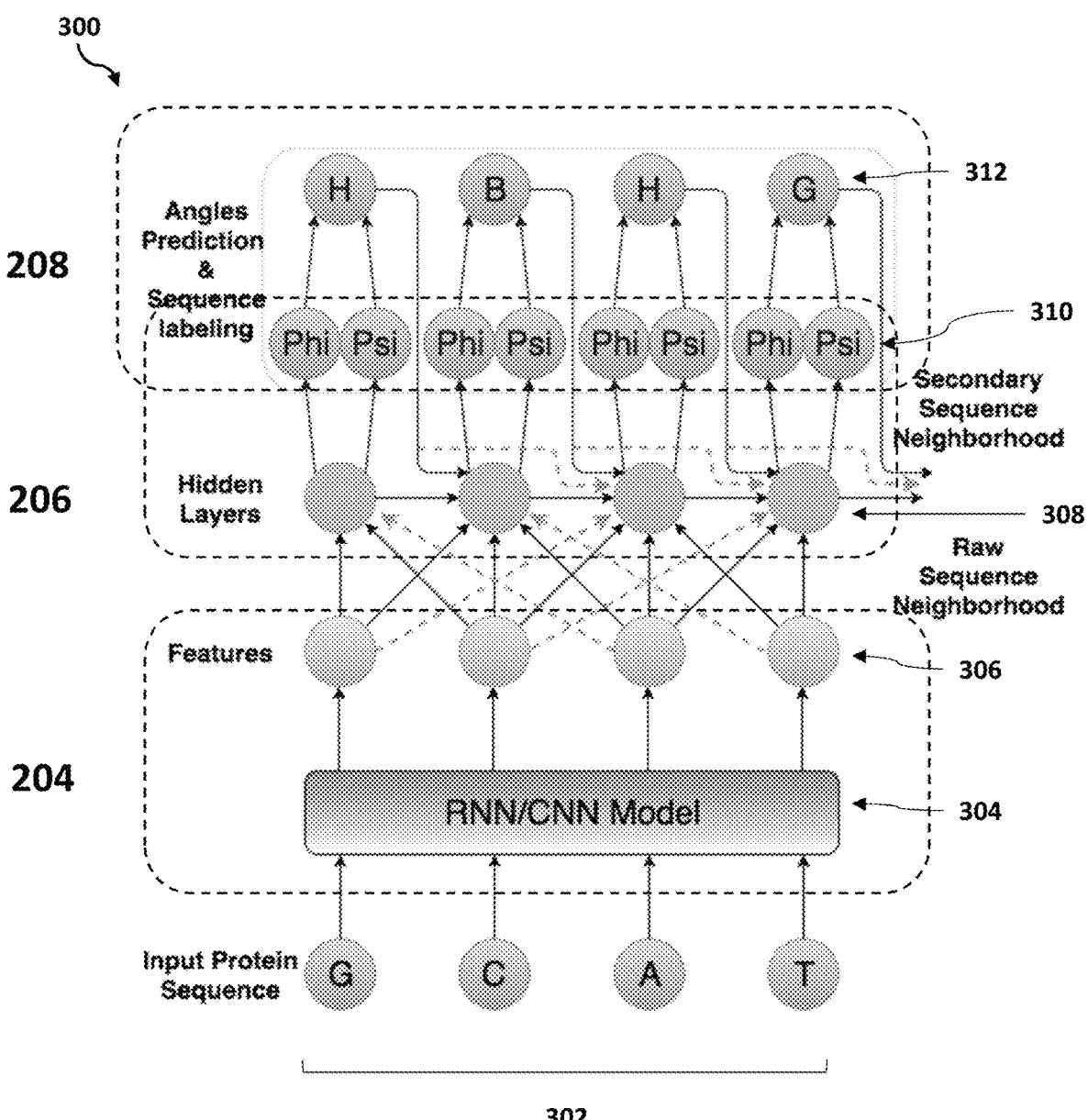
FIG. 3 is an operational flowchart illustrating a Multi-scale Neighborhood-based Neural Network (MNNN) model architecture for predicting dihedral angles according to at least one embodiment.

Referring now to FIG. 3, an operational flowchart of the MNNN model architecture for predicting dihedral angles 300 by the dihedral angles prediction program 110a, 110b is shown. The architecture of the MNNN model as shown in FIG. 3 incorporates the information of the raw sequence neighborhood and of the secondary sequence neighborhood. At 204, the dihedral angles prediction program 110a, 110b may compute character embedding 306 for each amino acid from the input protein sequence 302 by feeding the input protein sequence 302 into the RNN/CNN model 304. The computed character embeddings 306 may then be augmented with raw sequence neighborhood information to refined character embeddings 308. Next, at 206, the dihedral angles prediction program 110a, 110b may apply another LSTM layer (i.e., hidden layer) to predict the phi-psi angles 310 (i.e., dihedral angles) based on the refined character embeddings 308 to the input protein sequence 302 for each amino acid. Then, at 208, the dihedral angles prediction program 110a, 110b may utilize the refined character embeddings 308 to further predict secondary structure characters 312 as additional constraints based on the angles prediction and sequence labeling associated with the predicted dihedral angles 310.

Figure 4:
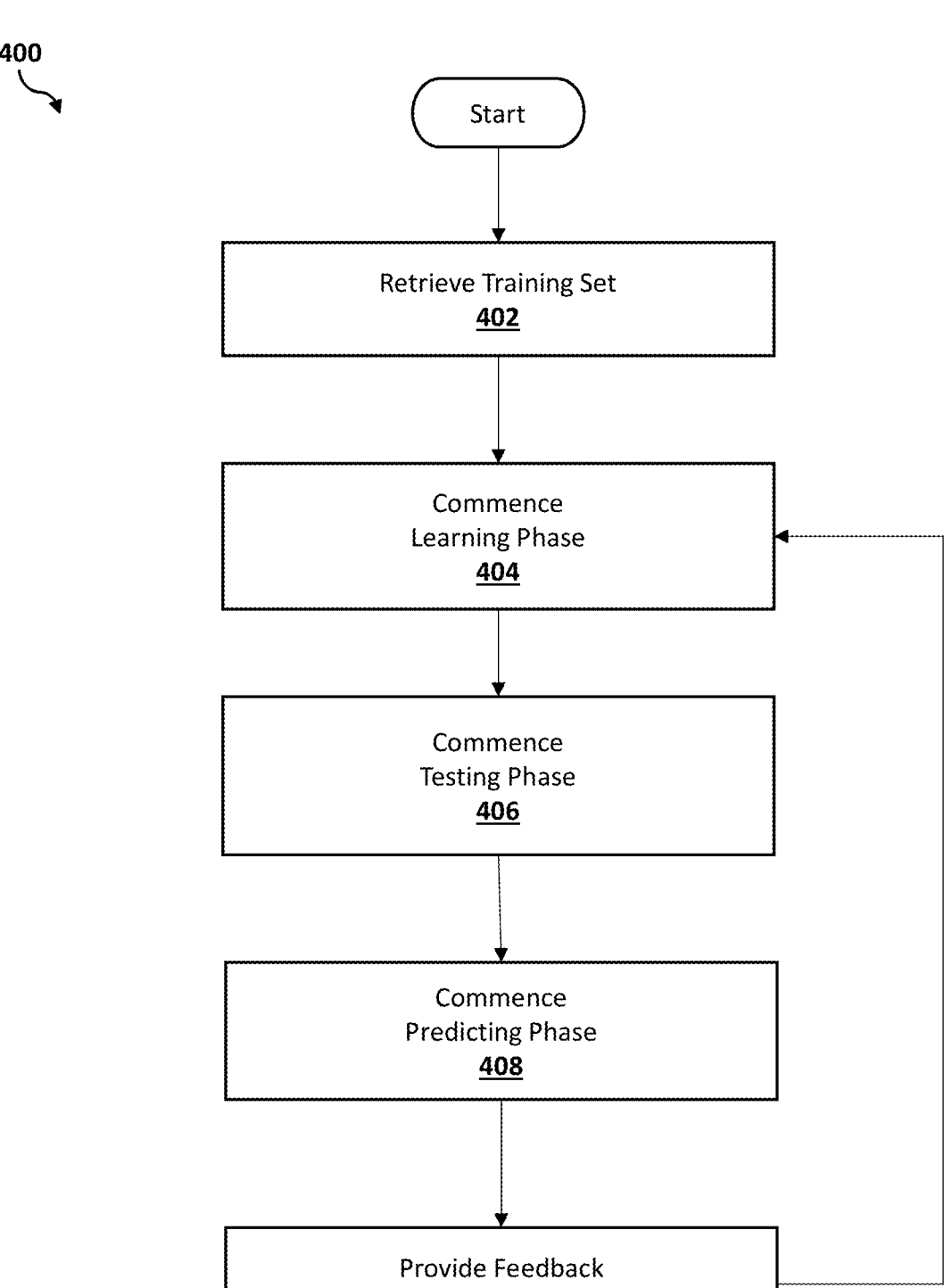
FIG. 4 is an operational flowchart illustrating the exemplary Multi-scale Neighborhood-based Neural Network (MNNN) model training process for predicting dihedral angles according to at least one embodiment.

Referring now to FIG. 4, an operational flowchart illustrating the exemplary Multi-scale Neighborhood-based Neural Network (MNNN) model training process 400 used by the dihedral angles prediction program 110a, 110b according to at least one embodiment is depicted.

At 402, a training set is retrieved. Utilizing the software program 108 on the user's device (e.g., user's computer 102), a training set from a protein data file (i.e., file) associated with a protein database (e.g., the Protein Data Bank (PDB), which may include more than 120,000 protein structures) may be transmitted as input into the dihedral angles prediction program 110a, 110b via a communication network 116.

Next, at 404, the learning phase is commenced. During the learning phase, the sequence data and the phi-psi angle data may be extracted for each protein data file for the high-resolution protein structure. The dihedral angles ($\varnothing(i)$, $\psi(i)$) for the amino acids of the known protein structures in the protein database may be computed. Then, the dihedral angles prediction program 110a, 110b may project (or label) the dihedral angles (i.e., known dihedral angles) to the center of domains by considering the natural distribution of ($\varnothing_p(i)$, $\psi_p(i)$) to reduce the degree of freedom. Then, a deep learning (DL) regression model (i.e., MNNN model) may be trained to recognize the hidden patterns between the protein sequence and the ($\varnothing_p(i)$, $\psi_p(i)$) or structural labels that are mapped to specific peptide sequences in each amino acid for proteins with the known 3D structures in the protein database.

Then, at 406, the testing phase is commenced. During testing phase, the DL model is tested to build the atomics structure for a protein with a known sequence. First, the DL model may be applied to a protein with a known or unknown sequence. Then, the DL model may predict the phi-psi angles ($\varnothing_x(i)$, $\psi_x(i)$) for any given protein sequence. The predicted angles, combined with raw sequence information, may then be translated to the backbone orientation to build the atomic 3D folded protein structure (i.e., folded structural protein), with intrinsic coordinates parameters, corresponding with the protein.

In at least one embodiment, the dihedral angles prediction program 110a, 110b may reduce the design space of backbone conformations while achieving a high fidelity and overall architecture of the MNNN model. The dihedral angles prediction program 110a, 110b may first utilize a K-means clustering algorithm to categorize the phi-psi angles in the PDB into a defined number of clusters (e.g., 256 clusters), which may effectively reduce the infinite combination of phi-psi angles to the value of one of the cluster center.

In the present embodiment, the testing phase may be utilized for inferencing the dihedral angles for any new amino acid sequence. The K-means clustering may be utilized to improve the existing categorization of the secondary structure information, by observations and experiments from physical science, instead of from the data itself. The better the categorization of the secondary structure information, the better the performance of the testing phase to improve the prediction of the dihedral angles.

Then, at 408, the predicting phase is commenced. During the predicting phase, the folded structural protein, which may serve as the input geometry, may be validated. First, the multi-stage predicting phase includes a long-time molecular dynamics (MD) simulations. The MD simulations may be run to quantify the acceleration of the MNNN model prediction and the stability of the folded structural protein, namely structural refinement. For example, the thermal stability of the predicted protein at room temperature may be tested. The folded structural protein may be validated by comparing the folded structural protein against the experimental synthesis (e.g., existing experimental data or using peptide synthesis). The structural features of the folded structural protein may then be characterized with other similar protein structures (e.g., characterization of the structural features in the folded structural protein and other similar protein structures).

In at least one embodiment, the dihedral angles prediction program 110a, 110b may utilized two force fields, namely CHARMM19 with implicit solvent and CHARMM17 with explicit solvent, with each of the force fields starting from two different extreme configurations (e.g., full extended chain, and a structure with phi-psi angles predicted from MNNN model) to perform individual long-time simulations for each of the protein sequence. During the simulation, the change of the molecular conformation may be benchmarked by quantitatively comparing with the corresponding protein structure (i.e., folded structural protein) within a protein database (e.g., PDB).

$$RMSD(t) =$$

$$\sqrt{\frac{\sum_{i=0}^{n} [(x_{i_{MD}}(t) - x_{i_{PDB}})^2 + (y_{i_{MD}}(t) - y_{i_{PDB}})^2 + (z_{i_{MD}}(t) - z_{i_{PDB}})^2]}{n}}$$

Where n is the number of the backbone atoms of each amino acid of the peptide and ($x_{i_{MD}}(t)$, $y_{i_{MD}}(t)$, $z_{i_{MD}}(t)$) is the Cartesian coordinates of the backbone atoms given by the MD simulation at time t, while ($x_{i_{PDB}}$, $y_{i_{PDB}}$, $z_{i_{PDB}}$) is the Cartesian coordinates of the backbone atoms of the protein structure within the protein database. In the CHARMM model, the mathematical formulation for the empirical energy function has the form:

$$E = \Sigma E_{bond} + \Sigma E_{angle} + \Sigma E_{dihedral} + \Sigma E_{improper} + \Sigma E_{Urey\text{-}Bradley} + \Sigma E_{nonbonded}$$

Each energy term may be given by $E_{bond}=K_{ij}(r-r_0)^2$ is the bond term that may define how two covalently bonded atoms interact in the stretching direction, $E_{angle}=K_{ijk}(\theta-\theta_0)^2$ is the angle term that defines how the angel among three covalently bonded atoms with one central atom changes under external force, $E_{dihedral}=K_{ijkl}[1+\cos(n\phi-\delta)]$ is the dihedral term that defines how the dihedral angle among four covalently bonded atoms with one central bond changes under external force, $E_{improper}=K_{ijkl}(\omega-\omega_0)^2$ is the improper angle term that defines how the improper angle among four covalently bonded atoms with one central atom changes under external force, $E_{Urey-Bradley}=K_u(u-u_0)^2$ is the Urey Bradley term that accounts for angle bending and $$E_{nonbonded} = \epsilon_{ij}\left[\left(\frac{R}{r_{ij}}\right)^{12} - \left(\frac{R}{r_{ij}}\right)^6\right] + \frac{q_iq_j}{r_{ij}\epsilon}$$

is the nonbonded term that accounts for the van Der Waals (VDW) energy and electrostatic energy. In all-atom force fields, water molecules generally may be treated either explicitly or implicitly for MD simulations.

In some embodiments, the dihedral angles prediction program 110a, 110b may use the CHARMM19 all-atom force field to model the atomic interactions for the straight chain and the MNNN predicted model. The solvent effect for this force field may be generally considered by using the implicit Gaussian model (EEF1) for the water solvent. The utilization of the implicit solvent model may accelerate the sampling speed of molecular configurations. The dihedral angles prediction program 110a, 110b may utilize the CHARMM c37b1 package to run the simulation for energy minimization and structural equilibration. The time step used for implicit solvent simulations is 1 fs.

Then, at 410, feedback is provided. The results of the predicting phase (e.g., MD simulations and the comparison and characterization) may be analyzed to determine whether there is any correlation between the existing experimental data or peptide synthesis, and the characterization of the structural features for the folded structural protein and the existing known data. The feedback may be automatically utilized by the dihedral angles prediction program 110a, 110b to improve the quality of the MNNN model. The feedback provided may create a robust computational basis that assists to select and verify the most promising sequences that may lead to alpha helix structures. After the feedback has been provided, the MNNN model training process 400 may then return to the learning phase 404 after the next training set is retrieved at 402.

In at least one embodiment, a user (or other human involved in the training of the MNNN model) may provide feedback to the dihedral angles prediction program 110a, 110b based on personal observations. Such feedback, similar to the feedback automatically generated by the dihedral angles prediction program 110a, 110b, may to utilize to improve the quality of the MNNN model.

Figure 5:
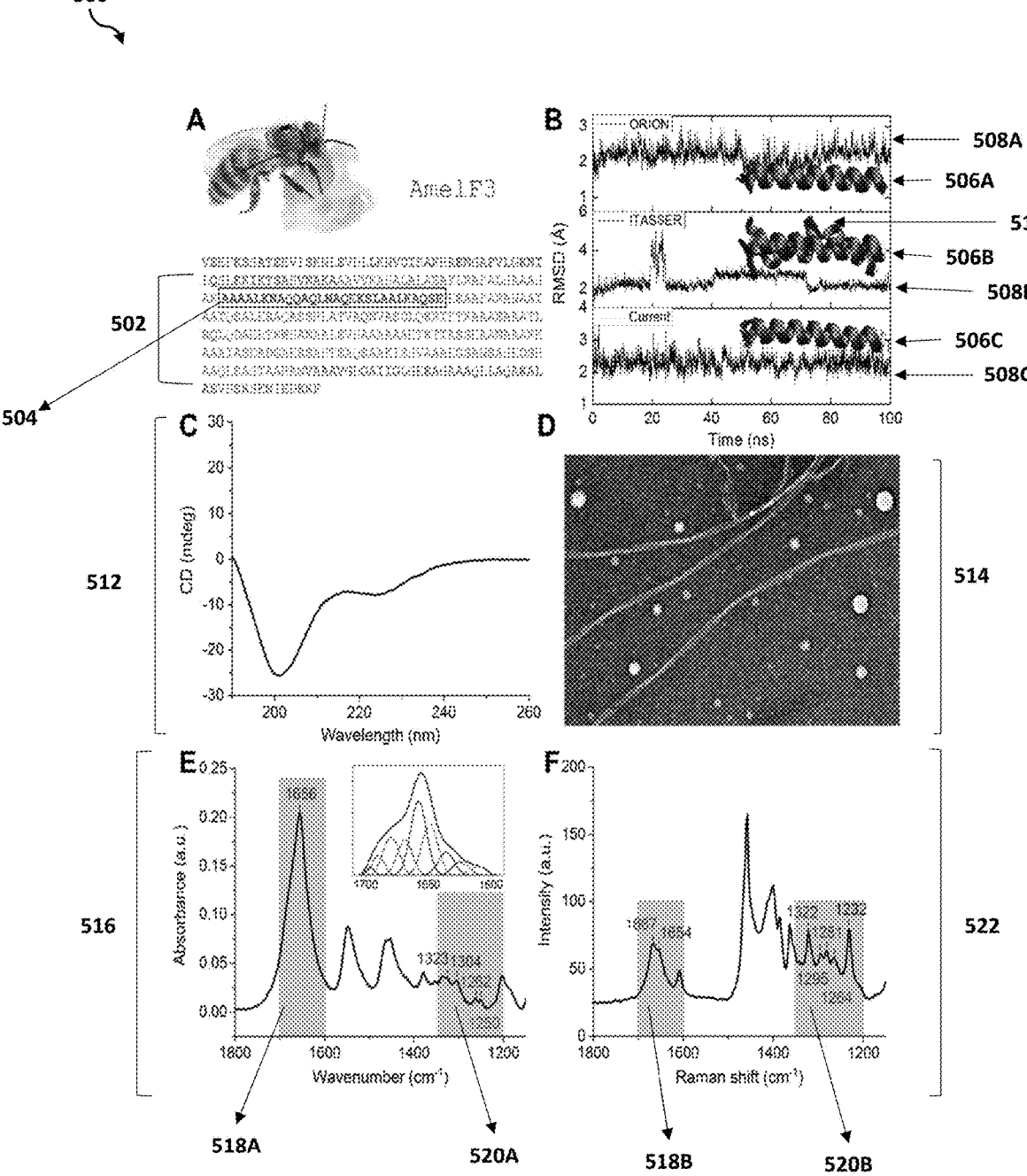
FIG. 5 is an exemplary diagram illustrating the synthesis and characterization of a de novo peptide sequence excluded from a protein database according to at least one embodiment.

FIG. 5 is an exemplary diagram 500 illustrating the synthesis and characterization of a de novo peptide sequence excluded from a protein database used by the dihedral angles prediction program 110a, 110b according to at least one embodiment is depicted.

The dihedral angles prediction program 110a, 110b may utilize the MNNN model in protein folding prediction on de novo proteins whose molecular structure is unknown. A peptide of amino acids may be extracted from the domain of a protein that was previously selected or retrieved by the dihedral angles prediction program 110a, 110b. The extracted peptide may be fed into the MNNN model as input. The results of the MNNN model (i.e., folded structural protein of the de novo protein) may be compared with structure homology prediction tools, such as Optimized Protein Fold Recognition (ORION) (i.e., a sensitive method based on a profile-profile approach that relies on a good description of the local protein structure to boost distant protein structure predictions) and Iterative Threading Assembly Refinement (I-TASSER (i.e., a hierarchical approach for protein structure and function prediction that identifies structural templates from the PDB, with full-length atomic models constructed by iterative template-based fragment assembly simulations). Each structure homology prediction tool and the MNNN model may build different folded structural proteins. The dynamic behaviors of the folded structural proteins may then be compared for structural refinement to obtain balance between the structure integrity and accuracy.

As shown in FIG. 5, an amino acid sequence of a honeybee silk protein, AmelF3, with a coiled coil domain 502 and a peptide (AmelF3_+1) sequence 504. The resulting AmelF3_+1 structure obtained by the MNNN model 506C is compared with predicted AmelF3_+1 structures obtained by structure homology prediction tools, namely the predicted AmelF3_+1 structure obtained by ORION 506A and the predicted AmelF3_+1 structure obtained by I-TASSER 506B. The three resulting AmelF3_+1 structures, obtained by ORION, I-TASSER and the MNNN model, were compared with dynamic behaviors in 100 ns MD simulation in explicit solvent (i.e., with snapshots taken every 20 ns of each simulation overlaid for comparison), 508A (ORION), 508B (I-TASSER) and 508C (MNNN model), respectively. Based on the dynamic behaviors, the AmelF3_+1 structure predicted by the MNNN model may be deemed as more thermodynamically stable than the predicted structures of ORION and I-TASSER. In particular, the AmelF3_+1 structure predicted by I-TASSER 506B, almost unfolded during the middle of the MD simulation, which was depicted by the unraveling the coiled structure 510.

In at least one embodiment, the AmelF3_+1 structured predicted by ORION may be further limited by template availability, and the prediction of the highest scoring structure may not be of the same length as the targeted sequence and one may have to find balance between the structure integrity and accuracy.

Additionally, to validate the computational results, the peptide may be synthesized and characterized experimentally by utilizing different experimental methods and tools (e.g., circular dichroism (CD) spectroscopy, Fourier-transform Infrared Spectroscopy (FTIR), Raman Spectroscopy, Transmission Electron Microscopy (TEM) imaging, molecular modeling, peptide synthesis).

As shown in FIG. 5, the peptide AmelF3_+1 was synthesized and characterized exponentially. The CD spectrum 512 of AmelF3_+1 to determine the secondary structures of the protein. The CD spectrum 512 compares CD in millidegrees (mdeg) with wavelengths in nanometers (nm) and depicts a major combination of alpha-helical, beta-turns and random coils conformations, with relative contents being 57%, 24% and 14% respectively, as estimated by the CONTIN/LL program. The potential peptide assembly into a higher-order structures was captured by TEM 514 in which the peptide assemblies into either nanofibers of around 10 nm in width and several microns in length or nanoparticles of diameters ranging from 10-35 nm.

The secondary structure analysis were independently confirmed by ATR-FTIR 516 and Raman spectroscopy 522 (e.g., infrared light is used to scan the test samples and observe the chemical properties), the spectra of which are complementary in the Amide I and III, with well-established peak assignments for different secondary structures. In 516, a major peak at 1656 cm-1 in the Amide I region 518A along with the two peaks at 1323 and 1304 cm-1 in the Amide II region 520A indicate predominant alpha-helical conformations of the AmelF3_+1 peptide. In 522, the Raman spectrum of AmelF3_+1 provides a similar structural information, with an Amide I region 518B and Amide II region 520B. Additionally, in 522, there were two more hidden alpha-helical peaks, 1295 cm-1 and 1281 cm-1, at 520B. As such, based on the results generated by dihedral angles prediction program 110a, 110b, with the correct buffer condition, more stable alpha-helical conformation of the AmelF3_+1 peptide may be achieved.

In the present embodiment, the MNNN model may be utilized for predicting the dihedral angles for any primary amino acid with known or unknown amino acid sequence. If the protein sequence is known, then the MNNN model may be validated, since the structure is also already known. If the protein sequence is unknown, then the MNNN model may accurately predict the dihedral angles for primary amino-acid, which may be used for further analyzing the corresponding 3D structured information associated with the protein.

FIG. 6 (SEQ NO ID. 1) illustrates the sequence listing of peptide AmelF3_+1, which may be extracted from the coiled coil domain of the honeybee silk protein.

The dihedral angles prediction program 110a, 110b may improve the functionality of the computer, the technology and/or the field of technology by building a MNNN model by learning the known protein structures, and further developing a MNNN model that utilizes no templates, co-evolution information, or structural biological knowledge to solve for the protein structure purely based on the raw amino acid sequence. The prediction accuracy may be further refined by incorporating new structures as new proteins are discovered on a daily basis, without affecting the predicting speed of the MNNN model since new data may only be inferred in the parameters in the neural network, without utilizing as templates during the prediction. The trained MNNN model created by the dihedral angles prediction program 110a, 110b may also predict dihedral angles with a high level of accuracy and efficiency with increased speed.

The dihedral angles prediction program 110a, 110b may include a data-driven approach to compute the possible number of secondary structure classes by utilizing a K-means clustering on PDB data with different cluster numbers and may verify the degree of matching in comparison with the benchmark PDB structure. The dihedral angles prediction program 110a, 110b may set the class number (e.g., 256) to reduce to a small level the error between the simulated structure and the benchmark result. Since the secondary structure of neighboring amino acids may influence the subsequent secondary structure of the next amino acid, the neighboring K number of secondary structure prediction information when predicting dihedral angles of the next amino acid. When training a MNNN model, both data embeddings representing the raw amino acid sequence and the secondary structure may be incorporated to learn final character embeddings. The dihedral angles prediction program 110a, 110b may then utilize the final character embeddings of the neighboring amino acids for phi-psi dihedral angle predictions of a given sequence of amino acids.

Furthermore, the artificial intelligence approach utilized by the dihedral angles prediction program 110a, 110b to design new proteins may open the door to generative methods that may complement conventional protein sequence design methods. For example, this approach may be used to design a long sequence that may yield the desired distribution of alternative helical and coil domains to assembly int functional channels for delivery of matters, and may achieve broader and more comprehensive structure prediction capacity, especially in other secondary structures.

In this embodiment, the dihedral angles prediction program 110a, 110b may include an end-to-end protein sequence to angle prediction model in which phi-psi dihedral angles may be predicted, and not merely domains without the inclusion of any cost metrics.

It may be appreciated that FIGS. 2-6 provide only an illustration of one embodiment and do not imply any limitations with regard to how different embodiments may be implemented. Many modifications to the depicted embodiment(s) may be made based on design and implementation requirements.

Figure 7:
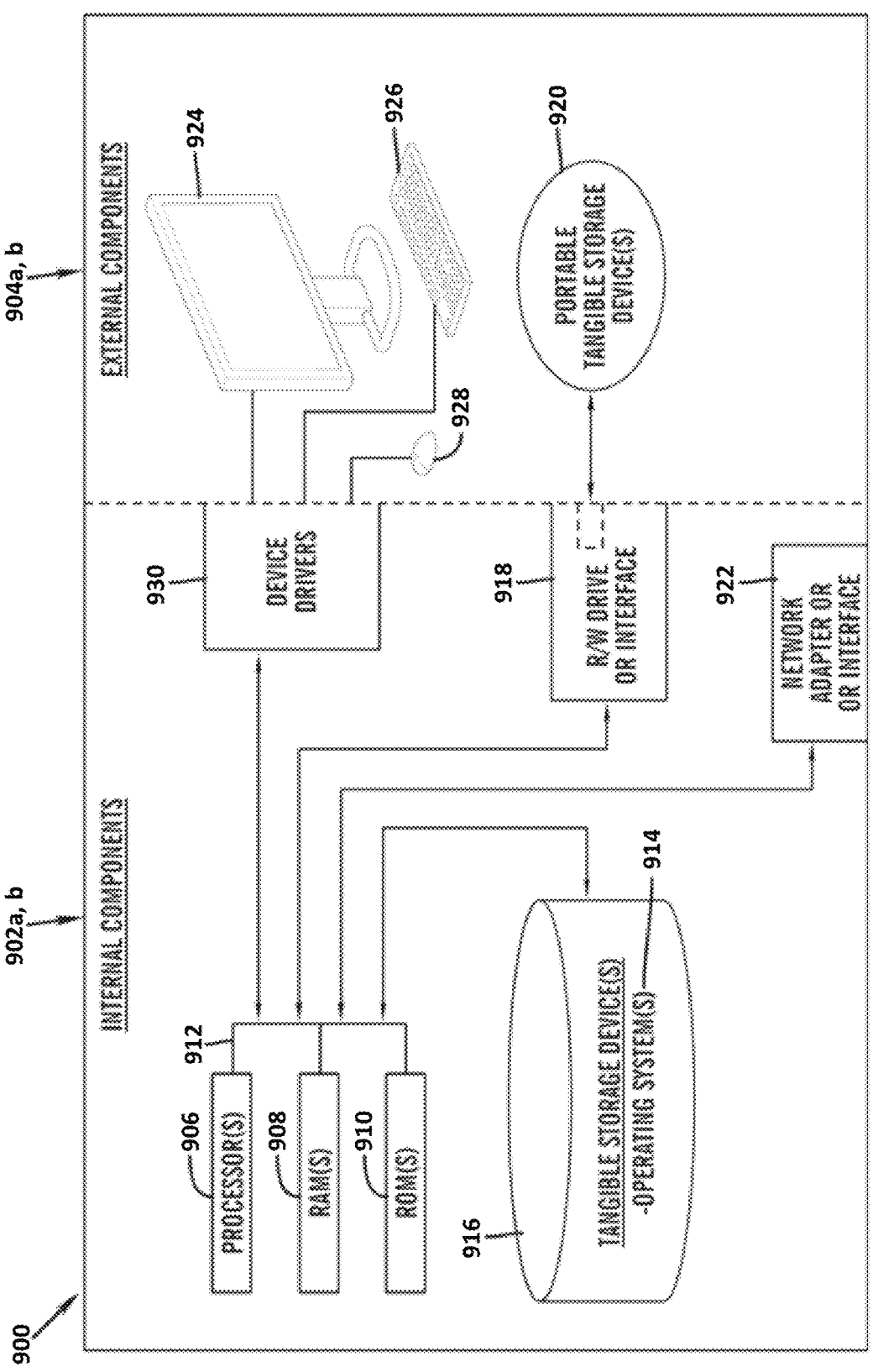
FIG. 7 is a block diagram of internal and external components of computers and servers depicted in FIG. 1 according to at least one embodiment.

FIG. 7 is a block diagram 900 of internal and external components of computers depicted in FIG. 1 in accordance with an illustrative embodiment of the present invention. It should be appreciated that FIG. 7 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may be represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902a, b and external components 904a, b illustrated in FIG. 7. Each of the sets of internal components 902a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108, and the dihedral angles prediction program 110a in client computer 102, and the dihedral angles prediction program 110b in network server 112, may be stored on one or more computer-readable tangible storage devices 916 for execution by one or more processors 906 via one or more RAMs 908 (which typically include cache memory). In the embodiment illustrated in FIG. 7, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the dihedral angles prediction program 110a, 110b can be stored on one or more of the respective portable computer-readable tangible storage devices 920, read via the respective R/W drive or interface 918 and loaded into the respective hard drive 916.

Each set of internal components 902a, b may also include network adapters (or switch port cards) or interfaces 922 such as a TCP/IP adapter cards, wireless wi-fi interface cards, or 3G or 4G wireless interface cards or other wired or wireless communication links. The software program 108 and the dihedral angles prediction program 110a in client computer 102 and the dihedral angles prediction program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the dihedral angles prediction program 110a in client computer 102 and the dihedral angles prediction program 110b in network server computer 112 are loaded into the respective hard drive 916. The network may comprise copper wires, optical fibers, wireless transmission, routers, firewalls, switches, gateway computers and/or edge servers.

Each of the sets of external components 904a, b can include a computer display monitor 924, a keyboard 926, and a computer mouse 928. External components 904a, b can also include touch screens, virtual keyboards, touch pads, pointing devices, and other human interface devices. Each of the sets of internal components 902a, b also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Analytics as a Service (AaaS): the capability provided to the consumer is to use web-based or cloud-based networks (i.e., infrastructure) to access an analytics platform. Analytics platforms may include access to analytics software resources or may include access to relevant databases, corpora, servers, operating systems or storage. The consumer does not manage or control the underlying web-based or cloud-based infrastructure including databases, corpora, servers, operating systems or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 8:
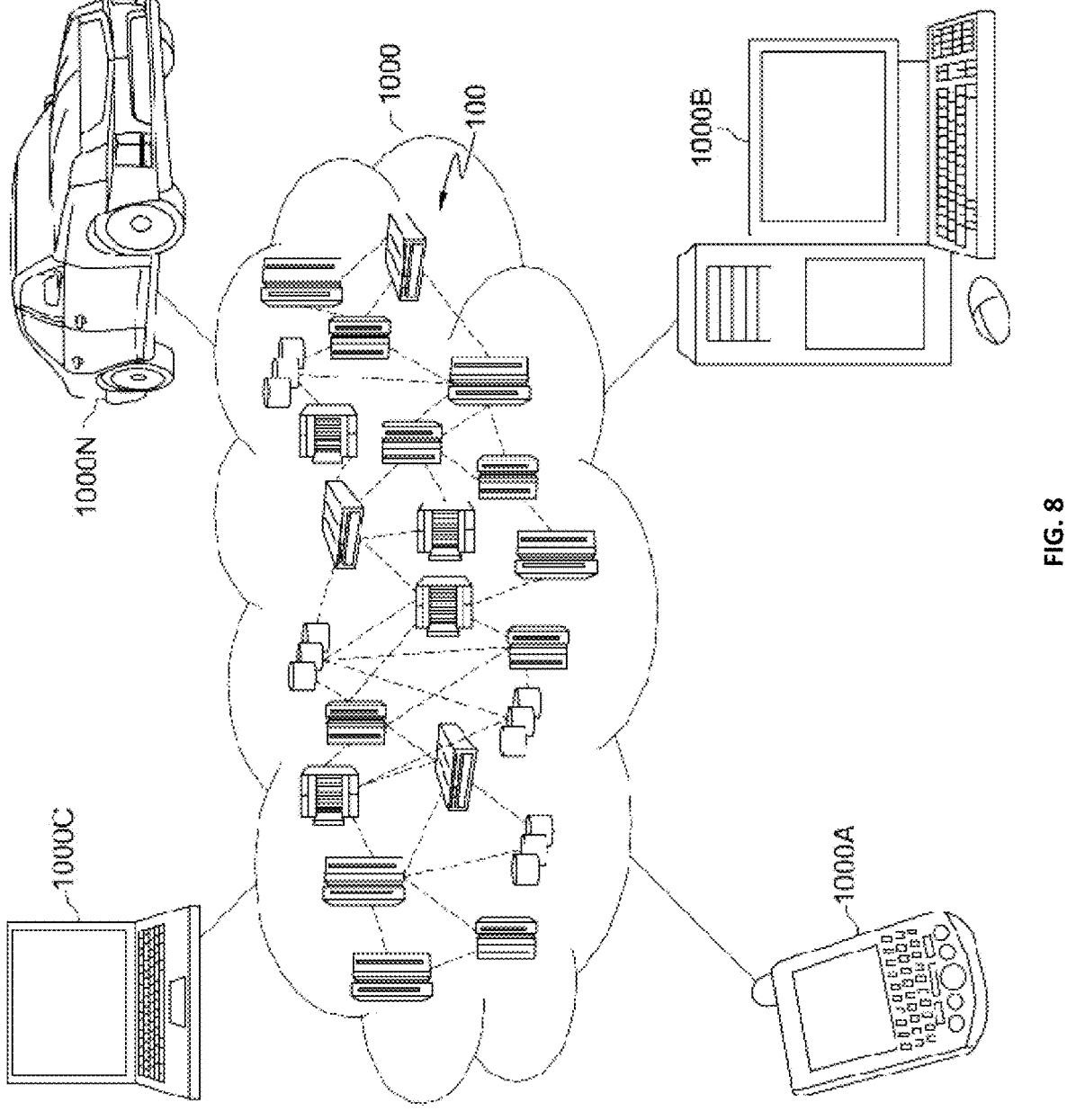
FIG. 8 is a block diagram of an illustrative cloud computing environment including the computer system depicted in FIG. 1, in accordance with an embodiment of the present disclosure.

Referring now to FIG. 8, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 8 are intended to be illustrative only and that computing nodes 100 and cloud computing environment 1000 can communicate with any type of computerized device over any type of network and/or network addressable connection (e.g., using a web browser).

Figure 9:
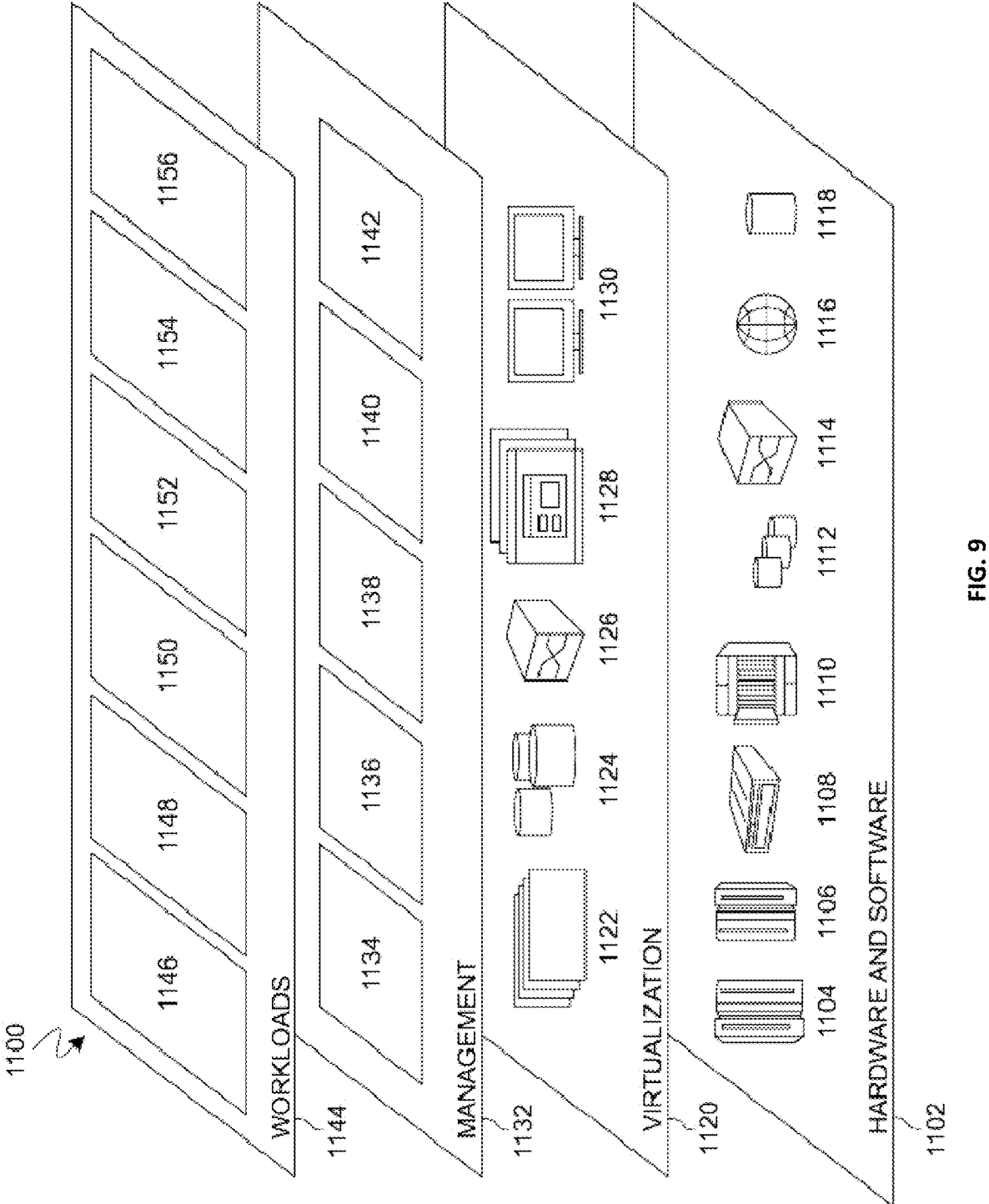
FIG. 9 is a block diagram of functional layers of the illustrative cloud computing environment of FIG. 8, in accordance with an embodiment of the present disclosure.

Referring now to FIG. 9, a set of functional abstraction layers 1100 provided by cloud computing environment 1000 is shown. It should be understood in advance that the components, layers, and functions shown in FIG. 9 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and dihedral angles prediction 1156. A dihedral angles prediction program 110a, 110b provides a way to predict accurate dihedral angles to accelerate the process of verifying structural stability of protein sequences.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:

obtaining at least one raw amino acid sequence;

computing one or more amino acid character embeddings based on the at least one raw amino acid sequence by utilizing a multi-scale neighborhood-based neural network (MNNN) model;

refining the computed one or more amino acid character embeddings with at least one set of sequence neighborhood information;

predicting one or more dihedral angles based on the refined one or more character embeddings; and simulating a protein structure based on the predicted one or more dihedral angles.

2. The method of claim 1, further comprising:

predicting at least one set of secondary structured information by utilizing a multilayer perception (MLP) layer of the MNNN model;

performing protein structural analysis based on the predicted at least one set of secondary structured information; and predicting one or more dihedral angles associated with at least one next amino acid.

3. The method of claim 1, further comprising:

generating an input request for a user, wherein input from the input request allows iterative user interaction in real-time to visualize the refined one or more character embeddings and the predicted one or more dihedral angles.

4. The method of claim 3, wherein generating the input request for the user for the iterative user interaction in real-time to visualize the refined one or more character embeddings and the predicted one or more dihedral angles, further comprises:

receiving at least one piece of feedback on the predicted one or more dihedral angles by one or more experts; and modifying the MNNN model based on the received at least one piece of feedback.

5. The method of claim 1, further comprising:

implementing one or more protein structural analysis based on the predicted one or more dihedral angles.

6. The method of claim 1, further comprising:

transmitting at least one training set from at least one protein data file, wherein the at least one protein data file is associated with a known protein from a protein database;

extracting a set of sequence data and a set of phi-psi angle data from the at least one protein data file;

computing one or more known dihedral angles by analyzing a natural distribution of one or more phi-psi angles associated with the transmitted at least one training set;

projecting the one or more known dihedral angles to a center of domains to reduce a degree of freedom using the natural distribution of the one or more known dihedral angles; and building a MNNN model to recognize one or more hidden patterns in a protein sequence associated with the transmitted at least one training set and the one or more phi-psi angles, wherein the one or more hidden patterns are mapped to the protein sequence for each amino acid in one or more proteins with a known 3D structure in the protein database.

7. The method of claim 6, further comprising:

applying the built MNNN model to a second protein with a second 3D structure;

predicting the one or more phi-psi angles associated with the second 3D structure;

combining one or more raw sequence information and the predicted one or more phi-psi angles corresponding with the second 3D structure; and generating one or more folded structural proteins based on a translation of the combined one or more raw sequence information and the predicted one or more phi-psi angles corresponding with the second 3D structure to backbone orientation, wherein a plurality of intrinsic coordinates parameters is included with the generated one or more folded structural proteins.

8. The method of claim 7, further comprising:

quantifying an acceleration of the predicted one or more phi-psi angles for the second 3D structure and a level of stability associated with the generated one or more folded structural proteins, wherein the acceleration is quantified by running one or more molecular dynamics simulations; and validating the generated one or more folded structural proteins.

9. The method of claim 8, wherein validating the generated one or more folded structural proteins, further comprises:

comparing the generated one or more folded structural proteins with one or more experimental synthesis, wherein the one or more experimental synthesis is selected from the group consisting of existing experimental data and peptide synthesis data; and characterizing one or more structural features associated with the compared one or more folded structural proteins with a plurality of other similar protein structures.

10. The method of claim 1, wherein computing one or more character embeddings based on the at least one raw amino acid sequence by utilizing the MNNN model, further comprises:

computing the one or more character embeddings in an absence of at least one template, at least one piece of co-evolution information, and at least one piece of structural biological knowledge.

11. A computer system for designing one or more folded structural proteins from at least one raw amino acid sequence, comprising:

one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:

obtaining the at least one raw amino acid sequence;

computing one or more amino acid character embeddings based on the at least one raw amino acid sequence by utilizing a multi-scale neighborhood-based neural network (MNNN) model;

refining the computed one or more amino acid character embeddings with at least one set of sequence neighborhood information;

predicting one or more dihedral angles based on the refined one or more character embeddings; and simulating a protein structure based on the predicted one or more dihedral angles.

12. The computer system of claim 11, further comprising:

predicting at least one set of secondary structured information by utilizing a multilayer perception (MLP) layer of the MNNN model;

performing protein structural analysis based on the predicted at least one set of secondary structured information; and predicting one or more dihedral angles associated with at least one next amino acid.

13. The computer system of claim 11, further comprising:

generating an input request for a user, wherein input from the input request allows iterative user interaction in real-time to visualize the refined one or more character embeddings and the predicted one or more dihedral angles.

14. The computer system of claim 13, wherein generating the input request for the user for iterative user interaction in real-time to visualize the refined one or more character embeddings and the predicted one or more dihedral angles, further comprises:

receiving at least one piece of feedback on the predicted one or more dihedral angles by one or more experts; and modifying the MNNN model based on the received at least one piece of feedback.

15. The computer system of claim 11, further comprising:

implementing one or more protein structural analysis based on the predicted one or more dihedral angles; and generating the one or more folded structural proteins based on the implemented one or more protein structural analysis.

16. The computer system of claim 11, further comprising:

transmitting at least one training set from at least one protein data file, wherein the at least one protein data file is associated with a known protein from a protein database;

extracting a set of sequence data and a set of phi-psi angle data from the at least one protein data file;

computing one or more known dihedral angles by analyzing a natural distribution of one or more phi-psi angles associated with the transmitted at least one training set;

projecting the one or more known dihedral angles to a center of domains to reduce a degree of freedom using the natural distribution of the one or more known dihedral angles; and building a MNNN model to recognize one or more hidden patterns in a protein sequence associated with the transmitted at least one training set and the one or more phi-psi angles, wherein the one or more hidden patterns are mapped to the protein sequence for each amino acid in one or more proteins with a known 3D structure in the protein database.

17. The computer system of claim 16, further comprising:

applying the built MNNN model to a second protein with a second 3D structure;

predicting the one or more phi-psi angles associated with the second 3D structure;

combining one or more raw sequence information and the predicted one or more phi-psi angles corresponding with the second 3D structure; and generating one or more folded structural proteins based on a translation of the combined one or more raw sequence information and the predicted one or more phi-psi angles corresponding with the second 3D structure to backbone orientation, wherein a plurality of intrinsic coordinates parameters is included with the generated one or more folded structural proteins.

18. The computer system of claim 17, further comprising:

quantifying an acceleration of the predicted one or more phi-psi angles for the second 3D structure and a level of stability associated with the generated one or more folded structural proteins, wherein the acceleration is quantified by running one or more molecular dynamics simulations; and validating the generated one or more folded structural proteins.

19. The computer system of claim 18, wherein validating the generated one or more folded structural proteins, further comprises:

comparing the generated one or more folded structural proteins with one or more experimental synthesis, wherein the one or more experimental synthesis is selected from the group consisting of existing experimental data and peptide synthesis data; and characterizing one or more structural features associated with the compared one or more folded structural proteins with a plurality of other similar protein structures.

20. The computer system of claim 11, wherein computing one or more character embeddings based on the at least one raw amino acid sequence by utilizing the MNNN model, further comprises:

computing the one or more character embeddings in an absence of at least one template, at least one piece of co-evolution information, and at least one piece of structural biological knowledge.

21. A computer program product for designing one or more folded structural proteins from at least one raw amino acid sequence, comprising one or more computer-readable storage media and program instructions stored on at least one of the one or more tangible storage media, the program instructions executable by a processor to cause the processor to perform a method comprising:

obtaining the at least one raw amino acid sequence;

computing one or more amino acid character embeddings based on the at least one raw amino acid sequence by utilizing a multi-scale neighborhood-based neural network (MNNN) model;

refining the computed one or more amino acid character embeddings with at least one set of sequence neighborhood information;

predicting one or more dihedral angles based on the refined one or more character embeddings; and simulating a protein structure based on the predicted one or more dihedral angles.

22. The computer program product of claim 21, further comprising:

predicting at least one set of secondary structured information by utilizing a multilayer perception (MLP) layer of the MNNN model;

performing protein structural analysis based on the predicted at least one set of secondary structured information; and predicting one or more dihedral angles associated with at least one next amino acid.

23. The computer program product of claim 21, further comprising:

generating an input request for a user, wherein input from the input request allows iterative user interaction in real-time to visualize the refined one or more character embeddings and the predicted one or more dihedral angles.

24. The computer program product of claim 23, wherein generating the input request for the user for the iterative user interaction in real-time to visualize the refined one or more character embeddings and the predicted one or more dihedral angles, further comprises:

receiving at least one piece of feedback on the predicted one or more dihedral angles by one or more experts; and modifying the MNNN model based on the received at least one piece of feedback.

25. The computer program product of claim 21, further comprising:

implementing one or more protein structural analysis based on the predicted one or more dihedral angles; and generating the one or more folded structural proteins based on the implemented one or more protein structural analysis.

* * * * *

SEQUENCE LISTING

<160> NUMBER OF SEQ ID NOS: 1

<210> SEQ ID NO 1
<211> LENGTH: 314
<212> TYPE: PRT
<213> ORGANISM: Apis mellifera

```
<400> SEQUENCE: 1

Val Glu Glu Phe Lys Ser Ser Ala Thr Glu
1               5                   10

Glu Val Ile Ser Lys Asn Leu Glu Val Asp
            15                  20

Leu Leu Lys Asn Val Asp Thr Ser Ala Lys
            25                  30

Arg Arg Glu Asn Gly Ala Pro Val Leu Gly
            35                  40

Lys Asn Thr Leu Gln Ser Leu Glu Lys Ile
            45                  50

Lys Thr Ser Ala Ser Val Asn Ala Lys Ala
            55                  60

Ala Ala Val Val Lys Ala Ser Ala Leu Ala
            65                  70

Leu Ala Glu Ala Tyr Leu Arg Ala Ser Ala
            75                  80

Leu Ser Ala Ala Ala Ser Ala Lys Ala Ala
            85                  90

Ala Ala Leu Lys Asn Ala Gln Gln Ala Gln
            95                  100

Leu Asn Ala Gln Glu Lys Ser Leu Ala Ala
            105                 110

Leu Lys Ala Gln Ser Glu Glu Glu Ala Ala
            115                 120

Ser Ala Arg Ala Asn Ala Ala Thr Ala Ala
            125                 130

Thr Gln Ser Ala Leu Glu Arg Ala Gln Ala
            135                 140

Ser Ser Arg Leu Ala Thr Val Ala Gln Asn
            145                 150

Val Ala Ser Asp Leu Gln Lys Arg Thr Ser
            155                 160

Thr Lys Ala Ala Ala Glu Ala Ala Ala Thr
            165                 170

Leu Arg Gln Leu Gln Asp Ala Glu Arg Thr
            175                 180

Lys Trp Ser Ala Asn Ala Ala Leu Glu Val
            185                 190

Ser Ala Ala Ala Ala Ala Ala Glu Thr Lys
            195                 200

Thr Thr Ala Ser Ser Glu Ala Ala Asn Ala
            205                 210

Ala Ala Lys Lys Ala Ala Ala Ile Ala Ser
            215                 220

Asp Ala Asp Gly Ala Glu Arg Ser Ala Ser
            225                 230

Thr Glu Ala Gln Ser Ala Ala Lys Ile Glu
            235                 240

Ser Val Ala Ala Ala Glu Gly Ser Ala Asn
            245                 250

Ser Ala Ser Glu Asp Ser Arg Ala Ala Gln
```

-continued

```
              255               260

Leu Glu Ala Ser Thr Ala Ala Arg Ala Asn
              265               270

Val Ala Ala Ala Val Gly Asp Ala Ile Ile
              275               280

Gly Leu Gly Glu Glu Ala Gly Ala Ala Ala
              285               290

Gln Leu Leu Ala Gln Ala Lys Ala Leu Ala
              295               300

Glu Val Ser Ser Lys Ser Glu Asn Ile Glu
              305               310

Asp Lys Lys Phe
```